United States
Uzgiris

[11] 3,984,533
[45] Oct. 5, 1976

[54] ELECTROPHORETIC METHOD OF DETECTING ANTIGEN-ANTIBODY REACTION

[75] Inventor: Egidijus E. Uzgiris, Schenectady, N.Y.

[73] Assignee: General Electric Company, Schenectady, N.Y.

[22] Filed: Nov. 13, 1975

[21] Appl. No.: 631,727

[52] U.S. Cl. .............................. 424/12; 23/230 B; 23/253 R; 204/150 R; 204/299 R; 350/160 R; 356/105
[51] Int. Cl.² .................. G01N 27/26; G01N 33/16
[58] Field of Search ..................... 23/230 B; 424/12; 204/180 R, 299 R; 356/105; 350/160 R

[56] References Cited
UNITED STATES PATENTS

| | | | |
|---|---|---|---|
| 3,091,697 | 5/1963 | Armbrecht | 356/105 X |
| 3,708,402 | 1/1973 | Bean | 204/299 R |
| 3,732,014 | 5/1973 | Uzgiris | 356/102 |
| 3,762,877 | 10/1973 | Rains | 204/299 R X |
| 3,764,512 | 10/1973 | Greenwood | 204/299 R X |
| 3,766,048 | 10/1973 | Flygare | 204/180 R X |
| 3,783,117 | 1/1974 | Bean | 204/180 R |
| 3,793,180 | 2/1974 | Flower | 204/180 R X |
| 3,819,505 | 6/1974 | Parent | 204/299 R |
| 3,855,094 | 12/1974 | Teppo | 204/299 R X |
| 3,870,612 | 3/1975 | Flygare | 204/180 R |
| 3,873,432 | 3/1975 | Israel | 204/299 R X |

OTHER PUBLICATIONS

R. J. Cohen, Immunochemistry, 12, pp. 349–351, (Apr. 1975).
E. E. Uzgiris, Optics Communications, 6, pp. 55–57, (Sept. 1972).
Science, 153, pp. 80–82 (1966).
Nature, 218, pp. 1078–1079 (1968).

*Primary Examiner*—Morris O. Wolk
*Assistant Examiner*—S. Marantz
*Attorney, Agent, or Firm*—Marvin Snyder; Joseph T. Cohen; Jerome C. Squillaro

[57] ABSTRACT

A method of rapidly detecting presence of antibodies in a solution comprises depositing, on each of a plurality of microscopic particles, an antigen specific to the antibodies sought, and forming a dilute suspension of the particles in the solution to be examined. The suspension is stirred, and electrophoretic mobility of the particles is measured upon formation of the suspension and measured again at a subsequent time. Detection of a change in electrophoretic mobility of the particles between the two measurements indicates presence of the antibodies in the solution.

7 Claims, 1 Drawing Figure

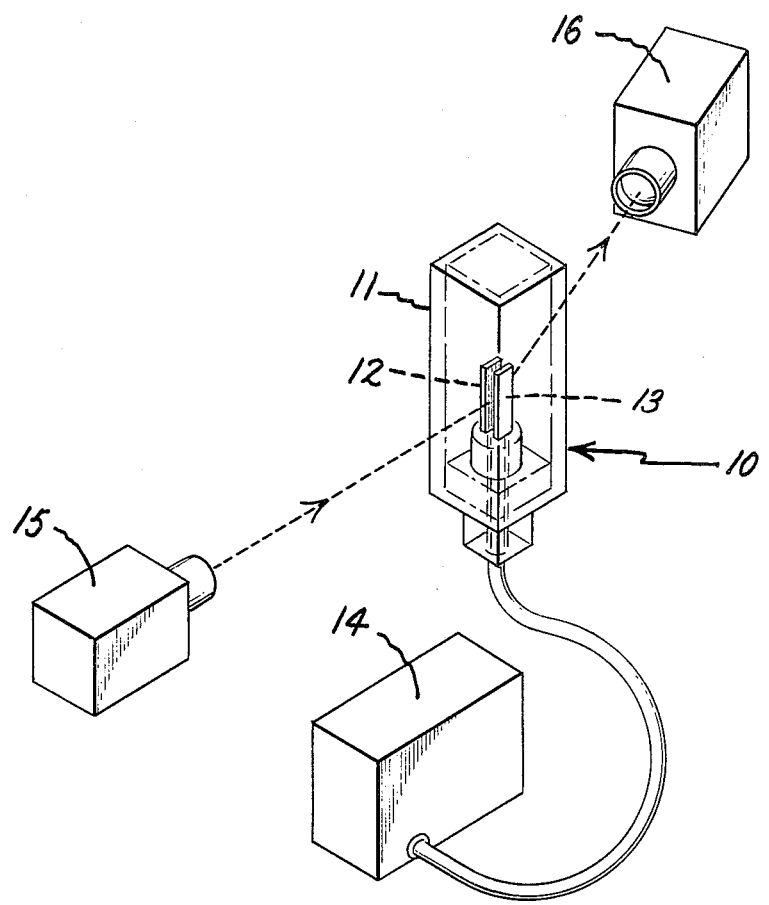

3,984,533

ELECTROPHORETIC METHOD OF DETECTING ANTIGEN-ANTIBODY REACTION

INTRODUCTION

This invention relates to detection of proteins, and more particularly to a method of rapidly detecting presence of specific antibodies in a solution.

Giaever application Ser No. 384,113, filed July 30, 1973, and assigned to the instant assignee, describes and claims an improved method and apparatus for detecting and purifying proteins and antibodies. As pointed out in the Giaever application, immunological reactions are highly specific biochemical reactions in which a first protein, denominated an antigen, combines with a second protein specific to the antigen, denominated an antibody, to form an immunologically-complexed protein. Immunological reactions within an organism, such as an animal, are vital to the animal in combating disease. Through a process not fully understood, entry of a foreign protein, i.e., the antigen, causes the organism to produce antibody proteins specific to the antigen. The antibody protein molecules have available chemical bonding sites which complement those on the antigen molecule so that the antigen and antibody chemically combine to form an immunologically-complexed protein.

The Giaever application points out that collection and purification of immunologically-active proteins has, in the past, depended upon the precipitating or agglutinating characteristic of the proteins resulting from the immunological complexing reaction. One example of such reaction has been the HCG protein pregnancy test. This test is performed by mixing a quantity of HCG anti-serum into a urine specimen. A plurality of polystyrene spheres which have been coated with HCG protein are then introduced into the previously-prepared urine specimen. The polystyrene spheres will agglutinate if, but only if, HCG protein is absent from the urine specimen, since the HCG protein on the polystyrene spheres will complex with the HCG anti-serum previously introduced in the specimen. However, if HCG protein is present in the urine specimen, the protein will complex with the previously-introduced HCG anti-serum so as to form a precipitate, thereby precluding availability of the anti-serum for complexing with the HCG protein on the spheres to cause the spheres to agglutinate.

The aforementioned Giaever application states that the HCG protein pregnancy test could be simplified by adhering HCG anti-serum onto the polystyrene spheres and directly testing a urine specimen. In such case, the spheres will agglutinate if, but only if, HCG protein is present in the specimen. The Giaever application, however, points out that this procedure has not been employed apparently because available HCG anti-sera are complex mixtures containing a large proportion of constituents other than HCG antibodies from the antisera. The Giaever application also notes, as another shortcoming of agglutination tests, that the particles involved may tend to agglomerate for any of a variety of reasons having nothing to do with immunological agglutination, thereby lowering reliability of the tests.

A discovery described in the Giaever application is that any arbitrary protein will adsorb onto a substrate in a monomolecular layer only, and that a specific antibody (or antigen) for such arbitrary protein will bond to the protein to form a bimolecular protein layer on the substrate. More particularly, a wafer of substrate material may be immersed in a solution of a first protein so that a monomolecular layer of the first protein will adhere to the substrate. The substrate thus coated is immersed in a second solution which may contain a second protein that specifically reacts with the first protein. The second protein, but only this protein, if present in the second solution will form a monomolecular layer overlaying the monomolecular layer of the first protein on the substrate. The coated substrate, after immersion in the second solution, is examined electrically or optically to determine whether a bimolecular or monomolecular layer of protein is adhering thereto, thereby signifying whether or not the second solution actually contains the second protein.

In accordance with the present invention, a first protein, or antigen, is deposited on microscopic particles. Such particles, thus coated, exhibit a certain electrophoretic mobility. If a protein which specifically reacts to the first protein, i.e., an antibody, is then combined with the first protein in a dilute solution of such antibodies, the electrophoretic mobility of the particle drops to a much lower value, since antibody molecules are of much lower mobility than most other proteins at normal pH of the solution. By properly adjusting pH, a substantial mobility difference is maintained between the antigen films, carried as a monomolecular layer on some of the particles, and the antigen-antibody films, carried as a bimolecular layer on others of the particles. This approach to detection of complexing lends itself to high sensitivity because mixing of the solution containing the particles and antibodies is a more efficient way of making contact therebetween than by bringing a protein solution into contact with a plane macroscopic surface. Also, detection of molecular layer formations on microscopic surfaces avoids insensitivities and other problems associated with agglutination detection. As an additional advantage, substantial particle surface coverage can be obtained in 10 to 20 minutes for concentration of protein in the nanogram per cubic centimeter range while, for macroscopic plane surfaces, the time period required to obtain comparable coverage with the same dilute protein concentrations is about 10 hours.

Accordingly, one object of the invention is to provide a method for rapidly detecting presence of a specific protein in a solution.

Another object is to provide a simple, highly sensitive method for detecting discrete molecular layer formations of proteins.

Another object is to provide an improved method of sensitively detecting a specific immune reaction.

Briefly, in accordance with a preferred embodiment of the invention, a method of detecting an antigen-antibody reaction comprises the steps of depositing an antigen on each of a plurality of microscopic particles, and forming a dilute suspension of the particles in a solution to be tested for presence of antibodies specific to the antigens on the particles. The suspension is stirred, and electrophoretic mobility of the particles is then measured.

BRIEF DESCRIPTION OF THE DRAWING

The features of the invention believed to be novel are set forth with particularity in the appended claims. The invention itself, however, both as to organization and method of operation, together with further objects and advantages thereof, may best be understood by reference to the following detailed description taken in conjunction with the accompanying drawing in which:

The FIGURE is an isometric view of apparatus that may be employed in practicing the method of this invention.

DESCRIPTION OF TYPICAL EMBODIMENTS

Preconditions for sensitivity of the detection method of the invention include selection of microscopic particles to be coated with a monomolecular protein layer, the particle concentration in solution, and mixing procedures. Particles comprising polystyrene spheres of 0.81 microns diameter, dialyzed to remove surfactants and other contaminants, have been employed successfully. However, the invention is not limited to polystyrene particles since other particles to which proteins will adsorb, such as silica particles, are also suitable. Most colloidal particles could, in principle, be suitable since there is no requirement on shape or uniformity of size, provided the specific gravity of the particles is chosen so that the particles remain in suspension for at least a few minutes to allow sufficient time for optical scattering measurements to be made. For adequate sensitivity, test particle solutions must be quite dilute since total particle surface area must be kept small (much less than one square centimeter, for example). Concentration of $10^6$ to $10^7$ particles per cubic centimeter, where the particles are of 0.81 microns diameter, have proven satisfactory.

High sensitivity may not necessarily be useful if it is accompanied by susceptibility to nonspecific effects, which generally occur in concentrated serum or protein solutions. In this instance, washing of the microscopic particles by centrifugation is sufficient to avoid nonspecific mobility changes which would otherwise be caused by exposure of the particles to such concentrated solutions. Presence of the second protein layer, if any, may then be detected with maximal sensitivity when the spheres are observed in a 0.005 Normal sodium chloride solution.

Mixing has been accomplished with use of conventional magnetic turbulent stirring in a beaker and by employing electrophoretic stirring in an optical cell. Electrophoretic stirring is especially useful since it results in motion of the microscopic particles relative to the immediate surrounding liquid. For optimal mixing, it may be best to combine turbulent and electrophoretic motion, the latter requiring a high enough electric field to produce electrophoretic motion.

The technique for detecting the antigen-antibody combination on a microscopic surface is dependent upon changes in electrophoretic mobility of particles which are protein-coated. A certain electrophoretic mobility is associated with a surface formed by an antigen deposited on a particle. If an antibody molecule is then made to combine with that protein, mobility of the particle drops to a considerably lower value, since antibody molecules are of much lower mobility than most other proteins at normal pH. Additionally, the pH may be adjusted within a range of about pH 4.0 to pH 8.0, so that a substantial mobility difference is maintained between the antigen and antigen-antibody films. Mobility of antigen-coated particles changes by as much as a factor of 2 or 3 when antibody molecules are made to combine with the antigen.

The electrophoretic mobilities are measured by detection of laser light that is scattered from the particles. The scattered light exhibits a shift in frequency as an electric field is applied to the particle solution, due to the Doppler effect and electrophoretic motion of the particles. This type of measurement, which is described by E. E. Uzgiris in "Electrophoresis of Particles and Biological Cells Measured by the Doppler Shift of Scattered Laser Light", *Optics Communications* 6 (September 1972) 55, allows even fractional coverage of the particle surface with antibody molecules to be readily observed. A substantial particle surface coverage can be obtained in 10 to 20 minutes for concentrations of protein in the nanogram per cubic centimeter range.

An optical Doppler electrophoresis measurement system for detecting mobility changes, such as described in the aforementioned Uzgiris *Optics Communications* article, is illustrated in the FIGURE. The system comprises an electrophoretic cell 10 including fluid containment means 11 fabricated of a light-transmissive, fluid-impenetrable material, such as glass, plastic or the like. A pair of closely-spaced electrodes 12 and 13 are included in cell 10. These electrodes are preferably of rectangular shape and have mutually parallel facing surfaces defining an interelectrode gap not exceeding 1 millimeter in width.

Container 11 is filled with a dilute colloidal suspension containing the microscopic particles having a layer of protein adsorbed thereon, and an electric field is established between electrodes 12 and 13 by power supply 14. The gap between electrodes 12 and 13 is illuminated by coherent optical energy from a laser 15. A portion of this energy is scattered by the microscopic particles within the gap between electrodes 12 and 13 and, because of the motion of the scattering particles in the electric field, exhibits a Doppler frequency shift. Energy scattered at a predetermined angle is received by optical detector 16 which is preferably a photomultiplier tube but may be any appropriate square law detector.

Detector 16 receives the Doppler-shifted energy scattered by the particles in suspension in the fluid inside container 11, and also receives unshifted energy scattered by fixed scattering objects, such as a wall of container 11. Since detector 16 receives both Doppler-shifted and unshifted energy, and is a square law detector, its output signal is indicative of the heterodyne product of the two frequencies received and hence may be analyzed by conventional techniques to determine electrophoretic mobility of the particles in cell 10 at two different times in order to detect a reduction in mobility that may have occurred between those two times.

The foregoing describes a method for rapidly detecting presence of a specific protein in a solution. The method is both simple and highly sensitive, functioning to detect discrete molecular layer formations of proteins. Specific immune reactions may be sensitively detected thereby.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

I claim:
1. The method of detecting an antigen-antibody reaction comprising the steps of:
 depositing an antigen on each of a plurality of microscopic particles;

forming a dilute suspension of said particles in a solution to be tested for presence of antibodies specific to the antigens on said particles;

stirring said suspension; and comparing electrophoretic mobilities of said particles at two different times.

2. The method of claim 1 wherein the step of stirring of said suspension comprises mixing said solution by electrophoretic motion.

3. The method of claim 1 wherein the step of stirring said suspension comprises mixing said solution turbulently and by electrophoretic motion.

4. The method of claim 1 wherein the step of comparing mobilities of said particles at two different times comprises detecting, at a predetermined scattering angle, laser light scattered by said particles and by a fixed light scatterer at each of said different times, analyzing the heterodyne product of the frequencies detected at each of said different times, and comparing the analyzed heterodyne products to obtain a measure of the changed mobilities of said particles between said different times.

5. The method of detecting a reaction between a first protein and a second protein comprising the steps of:

depositing said first protein on each of a plurality of microscopic particles;

forming a dilute suspension of said particles in a solution to be tested for presence of said second protein;

stirring said suspension; and detecting a reduction in electrophoretic mobility of said particles.

6. The method of claim 5 wherein the step of stirring said suspension comprises mixing said solution by electrophoretic motion.

7. The method of claim 5 wherein the step of stirring said suspension comprises mixing said solution turbulently and by electrophoretic motion.

* * * * *